(12) United States Patent
Harder et al.

(10) Patent No.: US 10,473,620 B2
(45) Date of Patent: *Nov. 12, 2019

(54) ANALYSIS OF ISOMERS IN TIMS-Q-Q-TOF MASS SPECTROMETERS

(71) Applicant: Bruker Daltonik GmbH, Bremen (DE)

(72) Inventors: Alexander Harder, Bremen (DE); Markus Lubeck, Bremen (DE); Sven Myer, Weyhe (DE); Detlev Suckau, Grasberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/238,989

(22) Filed: Jan. 3, 2019

(65) Prior Publication Data

US 2019/0154632 A1    May 23, 2019

Related U.S. Application Data

(63) Continuation of application No. 15/604,820, filed on May 25, 2017, now Pat. No. 10,317,362.

(30) Foreign Application Priority Data

Jun. 2, 2016  (DE) .................. 10 2016 110 165
May 22, 2017  (DE) .................. 10 2017 111 067

(51) Int. Cl.
*G01N 27/62* (2006.01)
*H01J 49/00* (2006.01)
*G01N 30/72* (2006.01)
*H01J 49/40* (2006.01)

(52) U.S. Cl.
CPC ....... *G01N 27/622* (2013.01); *G01N 30/7233* (2013.01); *H01J 49/004* (2013.01); *H01J 49/0031* (2013.01); *H01J 49/0045* (2013.01); *H01J 49/40* (2013.01)

(58) Field of Classification Search
CPC ...... H01J 49/004; H01J 49/0031; H01J 49/40; H01J 49/0045; G01N 27/622; G01N 30/7233
USPC ........................ 250/281, 282, 283
See application file for complete search history.

(56) References Cited

U.S. PATENT DOCUMENTS

2012/0273670 A1    11/2012  Park et al.
2017/0350861 A1*   12/2017  Harder .................. H01J 49/004

FOREIGN PATENT DOCUMENTS

WO    2013140132 A2    9/2013

* cited by examiner

*Primary Examiner* — Nicole M Ippolito
(74) *Attorney, Agent, or Firm* — Benoit & Côté Inc.

(57) ABSTRACT

The invention relates to methods for the detailed analysis of ion mixtures from complex mixtures of organic substances in time-of-flight mass spectrometers which are equipped with a trapped ion mobility spectrometer, a quadrupole mass selector and a fragmentation cell. The invention proposes to analyze ion signals of a first mass mobility map, fragment ion spectra and the identifications of the associated substances as to whether ion mixtures not resolved according to mass and mobility, for example from isomers or isobars, are possibly present, and to subsequently measure the ion signals of interest with method parameters which allow the ion species to be measured separately by means of high mobility resolution.

16 Claims, 8 Drawing Sheets

ANALYSIS OF ISOMERS IN TIMS-Q-Q-TOF MASS SPECTROMETERS

BACKGROUND OF THE INVENTION

Field of the Invention

The invention relates to methods for the mass spectrometric analysis of complex substance mixtures and in particular for the identification of isomers and isobars by means of time-of-flight mass spectrometers which are equipped with a trapped ion mobility spectrometer, a mass filter and a fragmentation cell.

Description of the Related Art

The U.S. Pat. No. 7,838,826 B1 (M. A. Park, 2008) discloses a trapped ion mobility spectrometer (TIMS), which is also called a trapped ion mobility separator hereinafter. In a trapped ion mobility spectrometer, ions inside a multipolar ion guide system are typically driven through a gas stream against an electric field barrier, which preferably has a ramp with increasing electric field strength. The ions gather along the ramp at positions where the gas friction for one ion species is in equilibrium with the restoring electric force in each case. The ions therefore gather, spatially separated according to their ion mobility. When sufficient ions have been stored, after a predetermined accumulation time, for example, the counter-acting electric field of the electric field barrier is lowered in a "scan", which causes the ions to be released sequentially from lower to higher mobility over the end of the ramp and to be transferred to a mass spectrometer, preferably a time-of-flight mass spectrometer with orthogonal ion injection.

Figure 1:
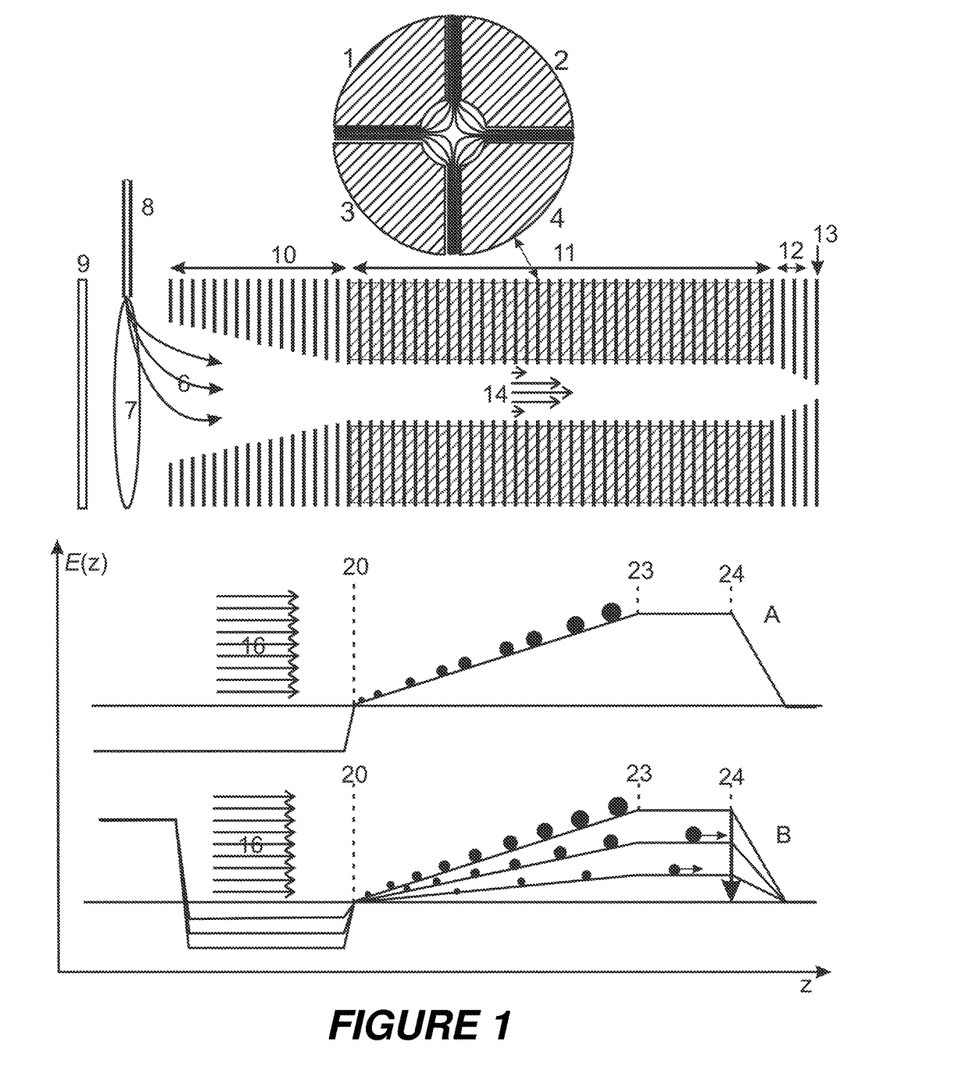
FIG. 1 shows a schematic representation of a typical trapped ion mobility separator and an operating mode of the trapped ion mobility separator.

FIG. 1 shows a schematic representation of a typical trapped ion mobility separator and an operating mode of the trapped ion mobility separator. Gas (7) with entrained ions (6) enters the first vacuum stage of a mass spectrometer through a capillary (8). The ions (6) are pushed into an RF ion funnel (10) by an electrode (9) and guided to the tube (11) of the trapped ion mobility separator, which comprises segmented ring electrodes. An RF quadrupole field is generated in the tube (11), which keeps the ions close to the axis of the tube (11), by applying RF potentials with alternating phase to the quadrants (1, 2, 3, 4) of the ring electrodes. Moreover, an electric field E(z) having a ramp along which the electric field strength increases (between positions 20 and 23), and a flat top (between positions 23 and 24) is generated in the tube (11) by DC potentials at the ring electrodes. A gas flow (14, 16) with a laminar velocity profile pushes the ions towards the ramp. Ions with the same mobility gather at a position on the ramp where the gas friction is in equilibrium with the restoring force of the electric field. After a certain accumulation time (Diagram A), the DC voltages are decreased (Diagram B), and the ions can leave the tube (11) through the diaphragm (13) across the flat top in the sequence of their mobility.

The lowering of the counter-acting electric field (scan) typically takes between 20 and 250 milliseconds. The trapped ion mobility separator can be very compact. The tube (11) as the main part can have a length of only five centimeters, for example.

Figure 2:
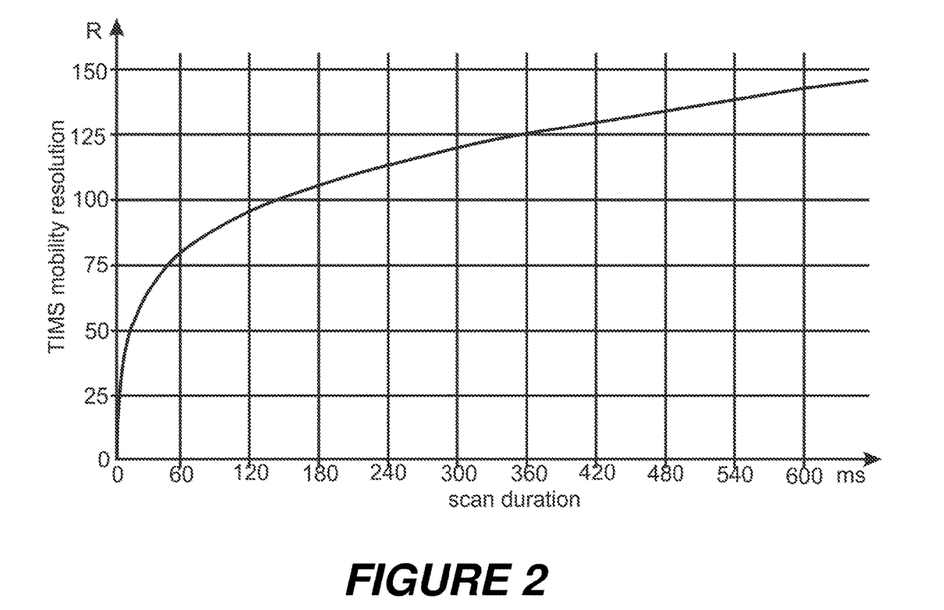
FIG. 2 shows the mobility resolution of a trapped ion mobility separator as a function of the scan duration.

This type of mobility spectrometer is unique in that the mobility resolving power depends on the scan speed. FIG. 2 shows the mobility resolution as a function of the scan duration. For ions with a mobility of around $K_0$=0.5, a mobility resolution of $R_{mob}=K_0/\Delta K_0=60$ is achieved with a scan duration of only 20 milliseconds; with a scan duration of 300 milliseconds, the mobility resolution increases to $R_{mob}$=120.

Figure 3:
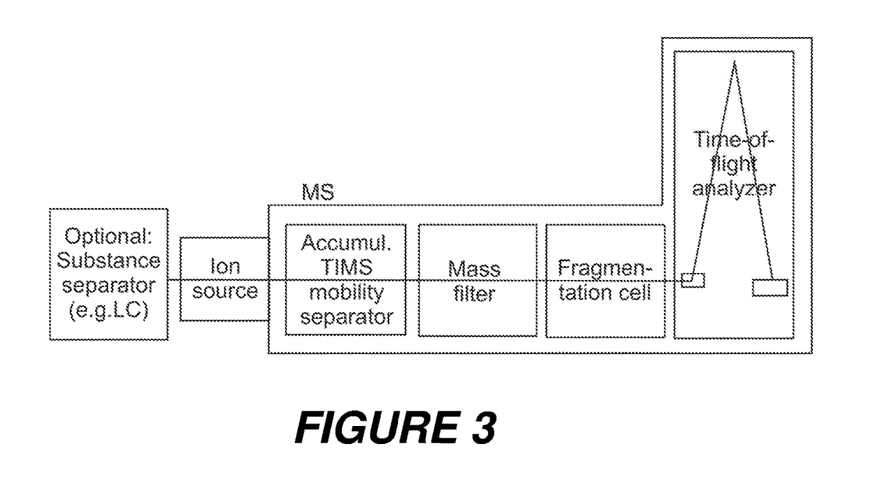
FIG. 3 shows a mass spectrometric system with which the methods according to the invention can preferably be carried out. The use of the trapped ion mobility separator (TIMS) with its adjustable mobility resolution allows analyses to be undertaken on individual ion species with highest mobility resolution.

The U.S. patent application Ser. No. 14/931,163 (M. A. Park et al.; "Acquisition of Fragment Ion Mass Spectra of Ions Separated by their Mobility"), which is incorporated herein by reference, describes a method to identify organic substances in a complex substance mixture, such as the enzymatic digest of a proteome. The method disclosed there is preferably conducted with a mass spectrometric system which is schematically depicted in FIG. 3 and comprises the following components: a liquid chromatograph (optional), an ion source, an (accumulative) trapped ion mobility separator, a mass filter, a fragmentation cell and a time-of-flight mass spectrometer with orthogonal ion injection and reflector.

The substances dissolved in a liquid are fed to an ion source, preferably an electrospray ion source, and ionized. Depending on the complexity of the substance mixture, the substances may already be chromatographically separated or may originate in unseparated form from a syringe pump.

Figure 4:
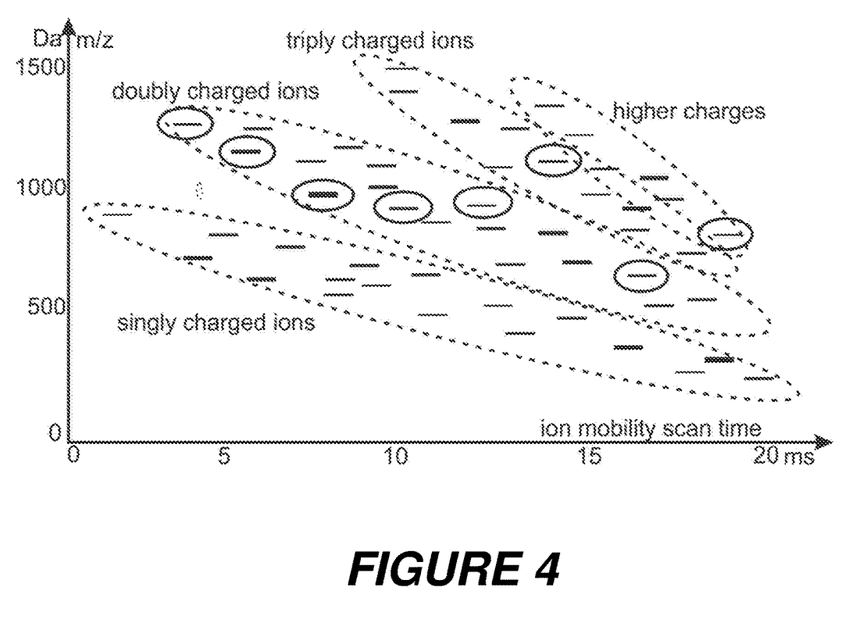

First a mass-mobility map, as shown schematically in FIG. 4, is acquired without using the mass filter and the fragmentation cell. Typically, the ions stored in the trapped ion mobility separator are separated according to their mobility in a mobility scan lasting around 50 milliseconds and transferred to the time-of-flight spectrometer, where the ion species, separated according to their mobility, are mass spectrometrically analyzed. A modern time-of-flight mass spectrometer can acquire 10,000 mass spectra per second, and it can be expedient to sum some of the acquired mass spectra in order to achieve a sufficiently good quality and a large dynamic range of signals.

For complex substance mixtures, the mass-mobility map comprises a large number of ion signals, which typically extend along the mobility axis for around one to three milliseconds. The mobility resolution here is much smaller than the mass resolution. The mass of the ion signals decreases along the mobility axis, and singly and multiply charged ions form strongly dispersed, partially overlapping bands (see FIG. 4). FIG. 4 is greatly simplified; on the one hand, it does not show the isotopic distributions of each ion signal, and on the other, the figure contains only relatively few ion signals—there can be thousands of ion signals for complex substance mixtures.

A first group of ion signals is then selected from the mass-mobility map. This group contains a number of ion signals which are arranged in temporal sequence, i.e. they do not overlap in the direction of the mobility axis. FIG. 4 shows a possible selection of a group of ion signals, which are encircled by ellipses in the mass-mobility map.

After the acquisition of the mass-mobility map and the selection of a first group of ion signals, a mobility scan is subsequently carried out to identify the substances of the ion signals of the group. The mass filter, the fragmentation cell and the time-of-flight mass spectrometer are needed for this purpose. After the trapped ion mobility separator has been filled and the mobility scan has started, the mass filter, usually a quadrupole mass filter, is switched to allow ions of the first ion signal from the group to pass through. It is preferable for all ions of the isotopic distribution to be included here in order to obtain fragment ion spectra whose isotopic distributions agree with those of reference spectra from spectral libraries. The mass filter is therefore set to a transmission window of a few daltons. The ions of the first ion signal thus selected according to mobility (scan time) and mass are fragmented in the fragmentation cell; the fragment ions are measured in the time-of-flight mass spectrometer as a fragment ion spectrum. As a rule, the substance can be identified from this fragment ion spectrum, usually via comparisons with reference spectra of a spectral library. In the further course of the same mobility scan, the ions of further ion signals are selected according to mobility and mass in the same way and fragmented. The time intervals between the ions of the group are chosen such that the mass filter can be switched to the mass of the ions of the subsequent ion signal. The further substances of the selected ion signals of this group are identified by acquiring the corresponding fragment ion spectra. The trapped ion mobility separator is then filled with a further batch of ions, and the identification of a second group of ion signals from the mass-mobility map can start.

If the mobility scan takes 20 milliseconds, for example, and an ion signal typically lasts 2.5 milliseconds on leaving the trapped ion mobility separator, then up to eight signals can be selected for each group in a single mobility scan; for a mobility scan lasting 50 milliseconds, each group can comprise around 20 signals. If a mass-mobility map comprises around 200 ion signals which are reasonably uniformly distributed, they can be split up into around 10 groups with a scan lasting 50 milliseconds. If they are not distributed uniformly, it may be necessary to form more than 10 groups in order to cover all signals of the mass-mobility map.

Several mass-mobility maps can be acquired and summed to improve the quality. It may furthermore be expedient, for larger molecules, to only select ion signals of ions which are at least doubly charged, since they can be fragmented more easily than singly charged ions and with a high yield.

Assuming a scan duration of 50 milliseconds each, around 20 of these measuring cycles can be completed, until after around one second a new mass-mobility map is measured, in order to take account of a change during a chromatographic separation, for example. Theoretically, around 400 ion species per second can be identified in this way. In reality, this number of measurements is not completely achieved, even when so many ion species are present. Even in very complex substance mixtures, it is usually not the case that so many ion species are available, however. The excess measuring capacity can then be used to measure weak ion signals in successive measurement cycles several times and to sum the fragment ion spectra in order to achieve a better quality of spectra and thus a more certain identification.

Figure 5:
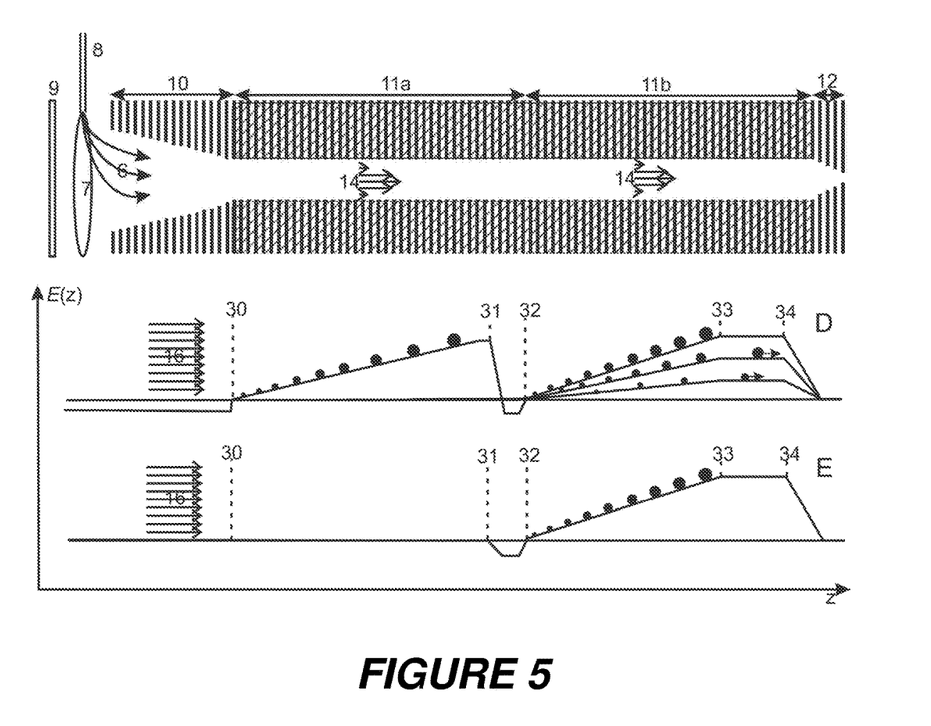
FIG. 5 shows a preferred operating mode of a trapped ion mobility separator with parallel accumulation.

This method can be modified in a variety of ways depending on the analytical requirements. A higher mobility resolution can be achieved by longer scan durations, while at the same time larger numbers of ion signals can be selected for each group. All ions of an ion source can be utilized by a trapped ion mobility separator with parallel accumulation of ions (U.S. patent application Ser. No. 14/614,456; "Trapping Ion Mobility Spectrometer with Parallel Accumulation", M. A. Park and M. Schubert) without ion losses occurring during the mobility scan. FIG. 5 illustrates a preferred operating mode of a trapped ion mobility separator with parallel accumulation. The extended tube (11) is subdivided into two regions (11a) and (11b) here. Ramps with increasing field strength can be set up in both regions, as can be seen in Diagrams D and E. The first region serves to accumulate ions, while the ions of the second region are being subjected to a mobility scan. When the mobility scan is finished, the ions of the first region can be transferred into the second region in around one millisecond.

"Isomers" are molecules which have the same elemental composition, i.e. the same molecular formula, but different primary structures ("structural isomers") or different secondary or tertiary structures ("conformational isomers"). Isomers have precisely the same mass. "Isobars" are different molecules which are composed of different elements such that their mass has the same number of atomic mass units (daltons), but not exactly the same mass. Isobars are then said to have the "same nominal mass". Molecular ions always have isotopic distributions which span several daltons. If the molecular ions of two molecules whose masses differ by only one, two or three daltons interfere with each other, it is not possible to separate the isotopic distributions of these molecules from each other with a mass filter. These molecules are called "near isobars" here. When the term "isomers" is used here, the expression is often to include the "isobars" or "near isobars" as well.

There is a need to have methods for analyzing complex substance mixtures which can be used to identify isomeric and isobaric organic substances in complex substance mixtures, in particular pharmacological substances of particular analytical interest, and to determine the mobility $K_0$ or the collision cross-section a of the substances as accurately as possible.

SUMMARY OF THE INVENTION

Experience has shown that not all ion signals of a mass-mobility map belong to single homogeneous ion species. Each ion signal can contain one ion species, but can occasionally also contain several isomers or isobars which are not resolved according to their mobility, and whose isotopic distributions overlap. Ion mixtures with sufficiently different mobility have already been resolved according to mobility by the known methods. Other ion mixtures contain ion species which are not resolved according to mobility.

The invention provides a method for analyzing a substance mixture in which a first mass-mobility map is acquired using a mass spectrometer which comprises a trapped ion mobility separator and a time-of-flight analyzer. The method is characterized by the fact that (a) an ion signal of interest is selected in the first mass-mobility map and examined as to whether it is a superimposition of signals from different ion species which are not sufficiently resolved according to mass or mobility, and that (b) a second mass-mobility map is acquired wherein at least one parameter of the trapped ion mobility separator is changed such that the region around the ion signal of interest is measured in the second map with a higher mobility resolution and/or mobility accuracy compared to the first map.

An "ion signal" is understood to be the signal of those ions which are released almost simultaneously from the trapped ion mobility separator during the mobility scan and transferred to the downstream mass analyzer.

The second, more detailed mass-mobility map is also called a "zoom map" hereinafter; it no longer contains all ion signals, but only the ion signals of the ion species selected in narrow mass and mobility ranges.

The invention provides a further method in which a first mass-mobility map is acquired using a mass spectrometer which comprises a trapped ion mobility separator, a mass separator, a fragmentation cell and a time-of-flight analyzer. Ion signals are selected from the first mass-mobility map and then fragment ion spectra of ions of the selected ion signals are acquired, wherein the ions are selected according to mobility and mass. The method is characterized by the fact that, in a first step, one of the selected ion signals, its fragment ion spectrum and/or the substance identification, is investigated as to whether this ion signal of interest is a superposition of signals of different ion species, which are not sufficiently resolved according to mass or mobility. In a second step, a second mass-mobility map is acquired wherein at least one parameter of the trapped ion mobility separator is changed for the analysis of the ion signal of interest such that the region around the ion signal of interest is measured in the second map with a higher mobility resolution and/or mobility accuracy compared to the first map. In the second step, additionally or alternatively, an additional fragment ion spectrum of ions of the ion signal of interest is acquired, wherein at least one parameter of the trapped ion mobility separator is changed such that the ions, selected according to mobility and mass, of the additionally acquired fragment ion spectrum have a smaller mobility bandwidth $\Delta K$ compared to those of the fragment ion spectrum acquired before.

The mass-mobility map from which the mobility or the collision cross-section and the mass of the ion signal are determined, and/or the fragment ion spectrum, can be used for the substance identification of the ion signals. The additional fragment ion spectrum is preferably used for the substance identification of the ion signal of interest. The mobility or the collision cross-section of the ion signal of interest can additionally or alternatively be determined from the second mass-mobility map and used for the substance identification of the ion signal of interest.

The ion signal of interest can be analyzed with regard to the signal width or signal form, or both, as to whether it is a superimposition of signals of different ion species. The signal width and/or the signal form of the ion signal of interest are preferably compared with the signal width or signal form of a single ion species and investigated in particular for a deviation along the mobility direction.

The at least one parameter of the trapped ion mobility separator which is changed in order to measure the region around the ion signal of interest with increased mobility resolution and/or increased mobility accuracy in the second map, is preferably the scan speed of the trapped ion mobility separator, in particular a reduction in the scan speed during the scan around the ion signal of interest. The scan speed of the trapped ion mobility separator can be reduced there as well in order to select ions with a smaller mobility bandwidth $\Delta K$ for the additional fragment ion spectrum.

The ion signal of interest is selected from the ion signals of the first map, using a selection list containing known isomers or isomers of particular analytical interest. The selection list here is preferably dependent on the type of substance mixture. The selection can be done by a user as well, however, who marks the ion signal of interest in a visual representation of the first map. The extent of the marking in the direction of mobility here can set the mobility resolution of the second map in the region of the ion signal of interest and specify the parameter(s) of the trapped ion mobility separator. It is preferable that only those ion signals are selected which have not already been selected and identified in a previous map.

The acquisition of the first and/or second map can involve a calibration of the mobility axis so that the mobility or the collision cross-section of the ion signal of interest can be determined. For the calibration, it is preferable if the known mobilities or collision cross-sections of identified substances of the substance mixture or of reference substances are used, the reference substances being added to the substance mixture. In particular, at least two reference substances whose mobilities encompass the mobility of the ion signal of interest can be added to the substance mixture.

The substance mixture can be fed to the ion source in dissolved form with a syringe pump, with the mass-mobility maps remaining essentially the same from measurement to measurement.

The substance mixture can also be first separated in a chromatograph and fed to the ion source as a separated substance mixture, however. The chromatography system is preferably a liquid chromatography (LC) system and the separated substance mixture is fed to the ion source in liquid form. The chromatography system (substance separator) can also be a gas chromatography system or carry out an electrophoretic separation, e.g. in the form of a capillary electrophoresis. For complex mixtures, a plurality of substances can still be superimposed even after a separation.

If the substances of the substance mixture are separated by means of a substance separator and fed to the ion source, the ion signals belonging to a substance only appear in mass-mobility maps being acquired in temporal sequence when the concentration of the substance has exceeded a sensitivity threshold. The concentration then increases initially in further mass mobility maps, reaches a maximum and decreases again. It is particularly favorable that an ion signal is only displayed in a visual representation of a mass-mobility map, or an ion signal of interest is only selected, when the ion signal has reached the maximum during the substance separation. Furthermore, an approximately constant concentration of the substance exists for a short time near the maximum.

If several samples with similar composition are to be separated and analyzed, for example always in the same way regarding the presence of specific isomers, then the optimum device parameters of the substance separator and/or the mass spectrometer can be determined for substances of interest in one or more cycles of a first sample and used for the samples subsequently analyzed. For a series of similar samples, the method according to the invention is therefore worked out in detail with the aid of a first sample and then used for the further samples in the same way. It is therefore expedient to save the device parameters which change during the separation process of the first sample and to re-use them later for further similar samples. At the known retention times of specific substances of interest, the corresponding device parameters of the mass spectrometer are used in particular, especially the corresponding device parameters of the trapped ion mobility separator, the mass filter, the fragmentation cell and/or the time-of-flight analyzer.

BRIEF DESCRIPTION OF THE DRAWINGS

FIG. 4 shows a schematic representation of a mass-mobility map which is acquired with the mass spectrometric system shown in FIG. 3, without the mass filter and the fragmentation cell being in operation. A group of eight ion signals, whose ions can be identified in a subsequent measuring cycle, is selected in the map. FIG. 4 is only a rough schematic of a mass-mobility map; many details are not visible here. Not shown, for example, is the fact that an isotopic distribution can be seen for each ion signal due to the high mass resolution of the time-of-flight mass spectrometer.

FIG. 10 depicts a constructed section of an LC chromatogram from second 900 to second 952, with several substance peaks which each have a full width at half-maximum of 10 seconds. Line (60) represents the sensitivity threshold. If one mass-mobility map is measured every second, represented by the vertical broken lines, the substance drawn as a broken line first appears at time t=929 s with intensity (61). In the subsequent mass mobility maps, the intensity increases from (62) to (68), with the intensity (68) lying at the start of the intensity maximum. A program-controlled analysis can determine when the maximum is reached for every substance, and offer only those substances which appear close to the maximum, and have not yet been identified in previous measuring cycles, for selection of the substances to be measured, as is shown in FIG. 4.

DETAILED DESCRIPTION

FIG. 4 shows a schematic representation of a mass-mobility map which is acquired with the mass spectrometric system from FIG. 3, without the mass filter and the fragmentation cell being in operation. A group of eight ion signals, whose ions can be identified in a subsequent measuring cycle, is selected in the map. FIG. 4 is only a rough schematic of a mass-mobility map; many details are not visible here. Not shown, for example, is the fact that each ion signal exhibits an isotopic distribution due to the high mass resolution of the time-of-flight mass spectrometer. In a visual representation of details of the map, an ion signal appears as a bunch of short horizontal lines, which can be recognized as bunches only at high screen zoom factor.

After the trapped ion mobility separator (TIMS cell) has been filled with sufficient ions, a mobility scan is started to identify selected ion signals. When the first ion signal appears at the exit of the trapped ion mobility separator, the mass filter is set to the mass of this ion signal and the ions are allowed to pass through the mass filter. The filtered ions are then fragmented in the fragmentation cell and the fragment ions are measured in the time-of-flight mass analyzer. It is usually possible to determine the substance of the ion signal from the fragment ion spectrum. The acquisitions of the fragment ion spectra of the second, third substance and so on then follow. When all eight ion signals of this signal group have been measured, the TIMS cell can be refilled and a second group of ion signals can be measured in a second measuring cycle.

The invention relates to a method for the detailed analysis of organic substances in complex mixtures which is conducted in a mass spectrometer comprising an ion source, a trapped ion mobility separator (TIMS), a mass separator, a fragmentation cell and a time-of-flight analyzer. In principle, mobility spectrometers can separate both isomers and isobars. They can usually separate near isobars as well.

In a first cycle, at least one mass-mobility map is acquired and selected ion signals from these maps are identified by the acquisition and evaluation of fragment ion spectra of the ions of these ion signals (first cycle).

The ion signals, their fragment ion spectra, their substance identifications and/or the identified substance structures are examined as to whether ion signals from these maps are possibly superpositions of different ion species which are not sufficiently resolved according to mass or mobility, and whether this means a mixture of isomers, isobars or near isobars is possibly present.

In a second cycle, further maps and/or fragment ion spectra are acquired, wherein detailed methods with changed method parameters are used in order to measure ion signals of analytical interest with increased mobility resolution or mobility accuracy, in particular in order to measure or select ions of analytical interest separately from other ion species. Detailed methods of the trapped ion mobility separator are particularly the temporal or spatial zoom. The mobility resolution or mobility separation selectivity around an ion signal of analytical interest can be higher than 100, preferably higher than 300, in particular higher than 500 here.

With many analytical methods it is not only important to detect groups with several isomers. If it is known that several isomers can be present for one substance of a substance group, and if only one isomer is found for this substance, it can be of particular analytical interest which isomer is present. For conformational isomers, in particular, the fragment ion spectra often only differ so slightly that a reliable identification of the isomer with the aid of this spectrum is not possible. If a complete group of isomers is found, then it is usually possible to determine the isomers by means of the structure of the isomeric group; this is usually not possible for an isomer that is individually present, however. If a fragment ion analysis does not give any indication of the identity of the isomer, the isomer can often be identified via a precise determination of the mobility or the collision cross-section.

Figure 6:
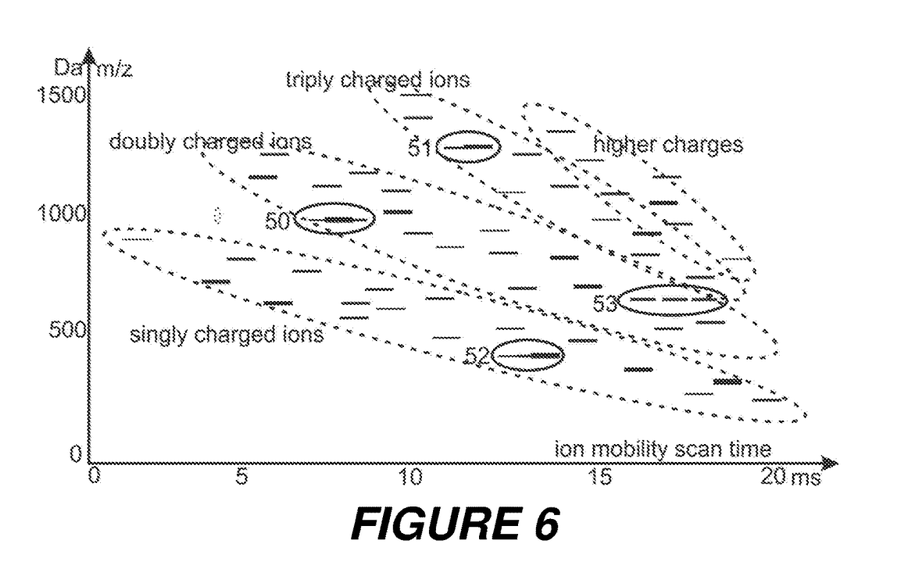
FIG. 6 shows a schematic representation of a mass-mobility map in which a series of ion signals (53) is resolved according to mobility. Further ion signals (50, 51, 52) comprise several ion species, but are not resolved according to mobility. If these ion signals are of particular analytical interest, they can be measured in a subsequent procedural step, resolved according to their mobility, particularly by using zooming methods.

FIG. 6 shows a schematic representation of a mass-mobility map in which a series of ion signals (53) is resolved according to mobility. Further ion signals (50, 51, 52) comprise a mixture of ions of several ion species, which are not resolved according to mobility, however. The presence of ion mixtures can often be detected via a temporally extended ion signal in the mobility direction, in particular if the map has already been acquired with a correspondingly high mobility resolution. The presence of ion mixtures often cannot be seen from the signal at all. If these ion signals are of particular analytical interest, they can be measured in a subsequent procedural step, resolved according to their mobility, particularly by using zooming methods.

The search for ion signals which are possibly unresolved signal superpositions of different ion species can be carried out in a variety of ways:

(a) Computer programs can automatically analyze the ion signals in the mass mobility maps, in particular their temporal width (signal width) and intensity distribution (signal form), and also overlaps of isotopic distributions.

(b) A user can examine the ion signals visually, and can be supported here by databases, which contain in particular those substance groups which frequently contain isomers. The databases here can in particular contain substance groups of particular analytical interest and be specific to the type of substance mixture under investigation.

(c) The fragment ion spectra should differ from each other, particularly in the case of isobars and near isobars, and facilitate the recognition of a mixture of different ion species. It is thus possible to identify ion mixtures with different numbers of double bonds.

(d) Substances which are identified in the map of the first cycle can also be examined as to the probability of the presence of isomers with the aid of databases, even without an analysis of the ion signals. Here as well, the databases can particularly contain substance groups, where the measurement of isomers is of particular analytical interest, or can be specific to the type of substance mixture under investigation. This means that ion signals whose signal forms and widths exhibit no peculiarities can also be included in the measurement of a second cycle. Some substance groups have a tendency to form isomers whose mobilities differ only very slightly, for example because with two isomers, a double bond can be located at two adjacent carbon atoms. These distinctions can particularly be of pharmacological importance. If only one isomer is present, it is often of particular interest to determine accurately which isomer it is.

(e) The at least approximately measured collision cross-sections a can be compared with library-type collections of substance data with their collision cross-sections in an automated way by computer programs, for example, and lead to more accurate measurements in the event of discrepancies.

It should be noted here that it does not always make sense for all ion signals which could contain isomers or isobars to be measured with increased mobility resolution in the second cycle also. Priority here should be given to the analytical significance.

It is not necessarily always only isomers or isobars which lead to ion signals which are a superposition of ion signals of different ion species and appear without being cleanly resolved according to mass and mobility. The mass filter is usually set such that the whole isotopic group is transmitted for one ion species; for heavier ions, the transmission width can optimally be around five daltons or more. This means that mixtures of ion species whose molecular masses differ by only a few daltons are no longer cleanly separated, however. If the molecules are very different, the mixture can be identified from the fragment ion spectra. They can also have nearly the same structure, however, for example when they have slightly different numbers of double bonds. Their molecular masses then each differ only by two, four or six daltons (for singly charged ions). Those mixtures of ion species with molecular masses which differ by only a few daltons can be separated by the method according to the invention in a second cycle with a correspondingly increased mobility resolution.

If ion signals are found for which a particular interest in a detailed analysis exists, the identification method can be performed a second time with the same substance mixture, but for each ion signal of interest, detailed methods are specifically set-up with specifically determined method parameters.

A temporal zoom is usually set here, which expands the mobility scan for the ion signals of analytical interest such that an enhanced mobility resolving power is achieved around these ion signals (see U.S. Pat. No. 8,766,176 B2; "Acquisition Modes for Ion Mobility Spectrometers using Trapped Ions", D. A. Kaplan et al.). How high the resolution has to be can often only be specified by experience or from information in suitable libraries. It is preferable if mobility resolutions of $R_{mob}$=150 to 250 are set.

If the ion signals can be superpositions, and if these ion signals are of sufficiently high analytical interest, then, after a renewed filling of the TIMS cell, further maps and/or fragment ion spectra are acquired, for which detailed methods with changed method parameters are used in order to measure the ion signals of analytical interest with increased mobility resolution or mobility accuracy, in particular in order to measure or select ions of analytical interest separately from other ion species The mobility resolution can be higher than 100, higher than 300, or even higher than 500, depending on the requirement. This second mass mobility map with increased mobility resolution will be called "zoom map" hereinafter.

Figure 7:
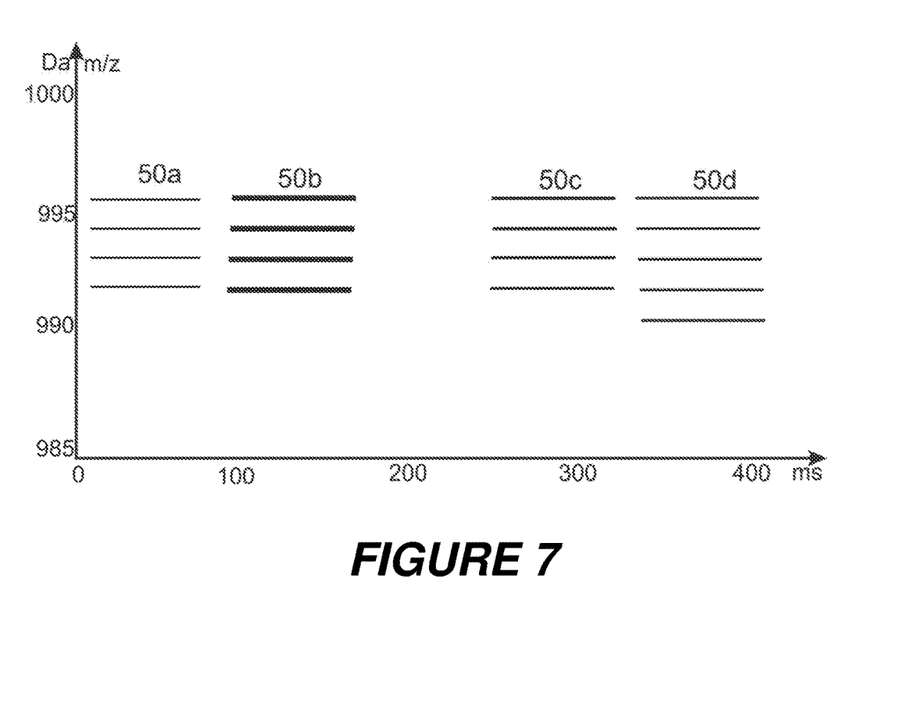
FIG. 7 shows a schematic representation of a second-mass mobility map (zoom map) of signal group (50) from FIG. 6, in which the mass range is limited to 15 daltons, and the mobility range of the signal group (50) is swept by a slow scan of 400 milliseconds. The signal group is now resolved according to mobility and also exhibits its isotopic structure in this representation. Signal group (50*d*) seems to be an isobar with a different isotopic composition.

Such a zoom map is shown in FIG. 7, albeit in a greatly simplified form. All intensities of the ions of every individual isotopic distribution are drawn identically here in order to make the difference between the isotopic distributions (50c) and (50d) visible. The zoom map depicts the signal group (50) of FIG. 6. It shows that the signal group (50) comprises four individual ion species, of which the fourth ion species (50d) is probably an isobar, since a different type of isotopic distribution is present. The zoom map shows only a mass range of 15 daltons and the mobility axis is expanded to 400 milliseconds by a temporal mobility zoom in order to achieve the high mobility resolution.

Several ion signals, which now usually represent individual ion species, i.e. isomers, isobars or near isobars, can then be selected again from the zoom map. In a further step of the method, fragment ion spectra of these ion signals can be acquired. The fragment ion spectra can be used for the identification of the now separated isomers, isobars or near isobars, although an unequivocal identification is not always achieved, because the fragment ion spectra of isomers can be very similar. If it is known that several isomers can be present for one substance of a substance group, and if only one isomer is found for this substance, it can be of particular analytical interest which isomer is present.

Figure 9:
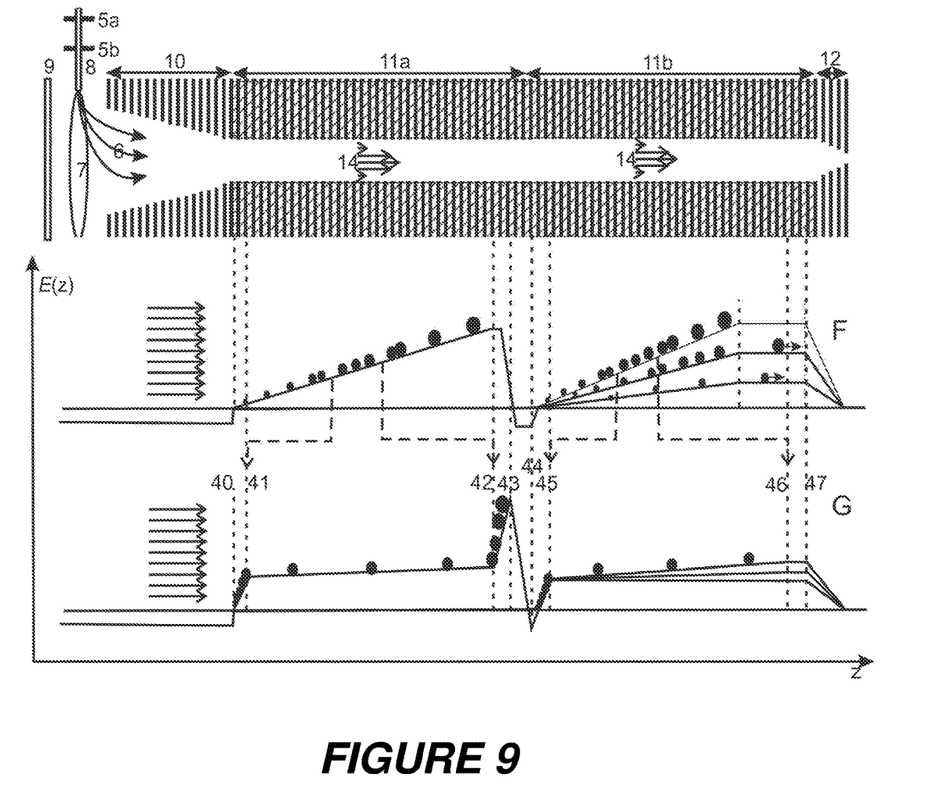
FIG. 9 shows a preferred operating mode of a trapped ion mobility separator with parallel accumulation, in which a "spatial zoom" is used to analyze a limited mobility range and minimize the effect of the space charge.

A temporal zoom can also be supported by a spatial zoom. FIG. 9 illustrates a preferred operating mode of a trapped ion mobility separator with parallel accumulation, in which a "spatial zoom" is used to analyze a limited mobility region and minimize the effect of the space charge and thus losses due to the space charge. For a spatial zoom, a ramp is set up in the storing part (11a) as well as in the scanning part (11b) by additional voltages at the electrodes of the tube, where a part of the ramp between positions (41) and (42) and between (45) and (46) respectively is kept very flat in order to store ions of a very small mobility range at large separations from each other. Many more ions can thus be stored in this mobility range, since the influence of the space charge on the ions is suppressed. This method is described in detail in U.S. patent application Ser. No. 14/931,125 (M. A. Park and O. Raether; "Spatial Zoom Mode for Accumulative Trapped Ion Mobility Spectrometry").

The determination of the optimal method parameters for the ion signals of analytical interest can be done automatically, for example in the case when the ion signal reveals a superposition structure in a mass mobility map of the first cycle. The mobility resolutions required for the ion signals of analytical interest can also be taken from libraries of isomers, if available. The ion signals of analytical interest can be noted in a list of the ion signals which are obtained from the first cycle. It is also possible to select the ion signals of interest simply in a representation of the mass-mobility map on a computer screen by marking the ion signals there, e.g. framed with a box. The size of the box can also specify the desired resolution here.

Figure 8:
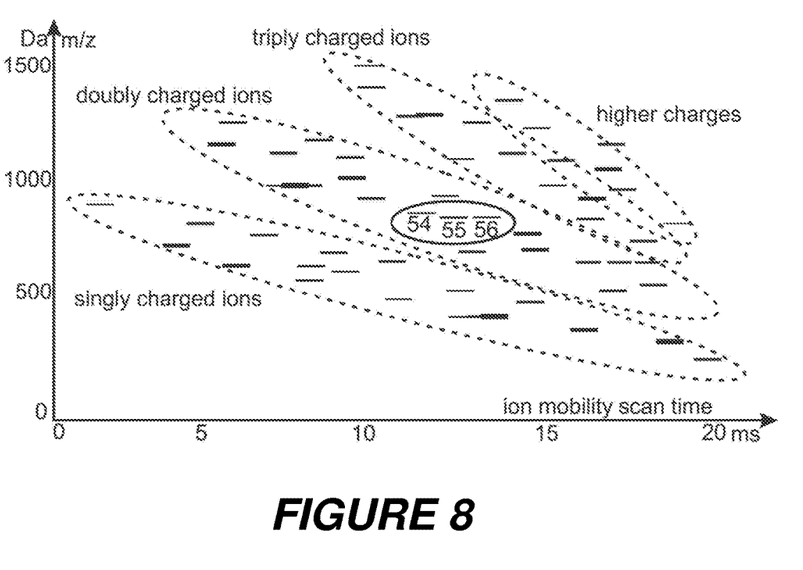
FIG. 8 shows a schematic representation of a mass-mobility map, in which an analyte signal of particular interest (55) is surrounded by two calibration signals (54) and (56) of accurately known mobility in order to determine the mobility of the analyte signal (55) accurately in a zoom scan.

If an accurate determination of the mobility $K_0$ or the collision cross-section a of a substance is of interest, reference substances (calibration substances) of accurately known mobility (or accurately known collision cross-sections) with similar or equal mass and only slightly different mobility can be added to the substance mixture especially for the second (or any further) cycle of the method. FIG. 8 shows a schematic representation of a mass-mobility map, in which an analyte signal of particular interest (55) is surrounded by two calibration signals (54) and (56) of accurately known mobility in order to determine the mobility of the analyte signal (55) accurately in a subsequent cycle with a temporal zoom. It is preferable to add at least two reference substances to both sides of the ion signal of analytical interest, if possible, so that the mobility of the ion signal and that of the two reference substances can be measured in a temporal zoom of a mobility scan. The mobility of the substance can then be interpolated with high accuracy and precision from this measurement. For a calibrated measurement, the known mobilities or collision cross-sections of already identified substances of the complex substance mixture can also be used, however.

The ion source depicted in FIG. 3 is preferably an electrospray ion source (ESI), to which the substances are fed in liquid form; other ionization types can also be used, however, such as thermospray ionization, chemical ionization or photoionization, each at atmospheric pressure after vaporization of the liquid which has been fed in, or Liquid Injection Field Desorption Ionization (LIFDI). The substances can be fed to the ion source in gaseous form as well, however, e.g. by coupling to a gas chromatograph, wherein the ionization can take place with the aid of electron impact ionization or chemical ionization, for example.

The substances can also be fed directly to the ion source as dissolved substances by a syringe pump or after separation by means of liquid chromatography or electrophoresis. A chromatographic pre-separation can take an hour or longer and provide a plurality of mass mobility maps with a few hundred thousand ion signals.

Figure 10:
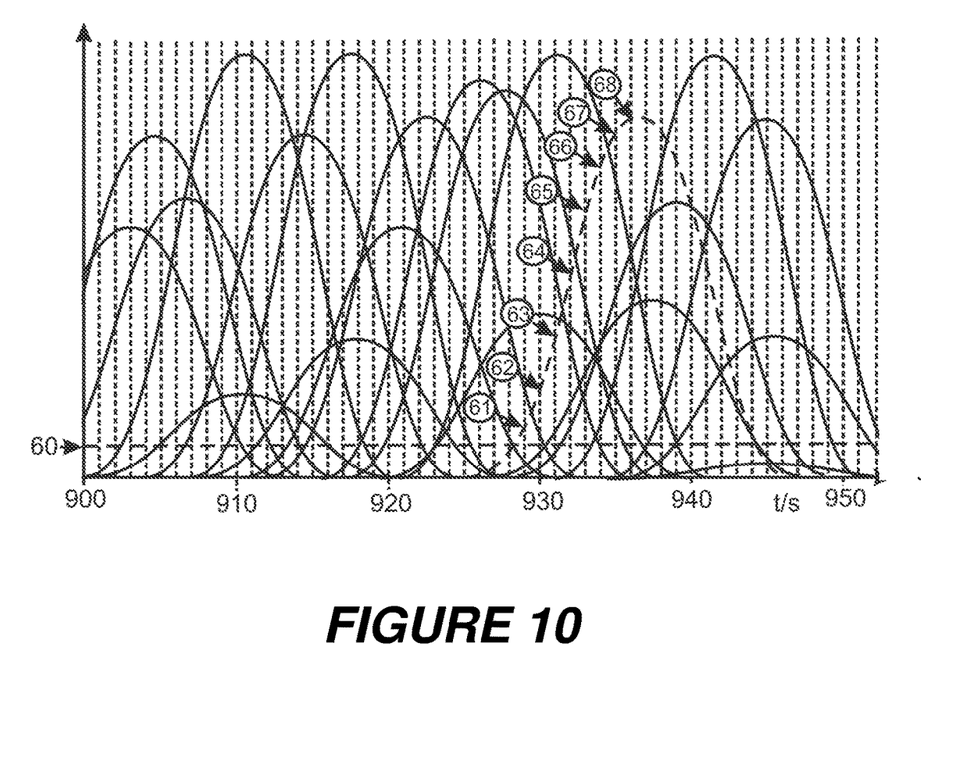

If the substances of the complex mixture are fed in after separation by chromatography or electrophoresis, the ion signals belonging to a substance appear in the mass-mobility maps acquired roughly once a second only when the concentration of the substance has exceeded a sensitivity threshold. FIG. 10 depicts a constructed section of an LC chromatogram from second 900 to second 952, with substance peaks which each have a full width at half-maximum of 10 seconds. Line (60) represents the sensitivity threshold. If one mass-mobility map is measured every second, represented by the vertical broken lines, the ion signal for the substance drawn as a broken line appears for the first time at time t=929 s and with intensity (61). In the subsequent mass-mobility maps, the intensity of this ion signal increases from (62) to (68), with the intensity (68) lying at the start of the intensity maximum. A program-controlled analysis can determine for each ion signal of the mass-mobility maps when the maximum is reached. It is then possible to only offer substances near the maximum for the selection of the ion signals whose fragment ion spectra are to be measured (see FIG. 4). The same also applies to ion signals which are to be subjected to a detailed analysis for isomers, isobars, or near isobars.

FIG. 4 can be construed in a completely new way when this procedure of limiting to maxima is applied: The ion signals of the mass-mobility map should only be those ion signals which are near the maxima of the LC peaks and which have not already been identified in earlier measuring cycles. This method helps to make the mass mobility maps for extremely complex substance mixtures more clear.

In the case of a pre-separation by means of liquid chromatography or electrophoresis, a calibration is difficult, since calibration substances usually elute at different times to the analyte substances. A calibration solution can be added, however, ideally in an automated way.

It should be noted here that series of analyses are often conducted on substance mixtures which are known to have nearly the same composition and are all subject to the same analytical objective. If a detailed method (second cycle) with satisfactory fine analyses of isomers, isobars or near isobars has been established for this type of substance mixture, it is not absolutely necessary to carry out the first cycle. A first cycle carried out once can be used as the basis for analyses of a specific type of substance mixture. If large numbers of samples with a similar type of composition are to be analyzed with the aid of a chromatographic or an electrophoretic separation, for example always in the same way for the presence of specific isomers, the detailed methods obtained and developed in first separation cycles of a first sample can run automatically in separations of further samples, whereby the parameters belonging to the given retention times are used. The proposal is therefore to save the parameter changes during the cycles and to re-use them later for similar samples.

If the mass spectrometer is equipped with computers with sufficient capacity and sufficient speed, and if corresponding programs can be provided, then the fully automatic measurement of mass-mobility maps, selection of groups of ion signals, measurement of the fragment ion spectra, selection of ion signals of particular analytical interest, measurement of zoom maps, and measurement of the fragment ion spectra of the now separated ion species in a single LC run is possible. If the ion signals of interest are selected with the aid of the user, then at least two LC runs are required, with the zoom maps being measured in the second LC run.

The invention claimed is:

1. A method for analyzing a substance mixture in a mass spectrometer which comprises a trapped ion mobility separator and a time-of-flight analyzer, wherein a first mass-mobility map is acquired, comprising the steps:
    (a) selecting an ion signal of interest in the first mass-mobility map and examining the selected ion signal of interest as to whether it is a superposition of signals from different ion species, and
    (b) acquiring a second mass-mobility map wherein at least one parameter of the trapped ion mobility separator is changed such that the region around the ion signal of interest is measured in the second map with a higher mobility resolution and/or a higher mobility accuracy compared to the first map.

2. The method according to claim 1, wherein a signal width or signal form, or both, of the ion signal of interest is examined as to whether it is a superposition of signals of different ion species.

3. The method according to claim 2, wherein the signal width or the signal form or both are examined regarding a deviation from the signal width or signal form of a single ion species.

4. The method according to claim 3, wherein a deviation between the ion signal of interest and the ion signal of a single ion species along the mobility direction is analyzed.

5. The method according to claim 1, wherein the at least one parameter of the trapped ion mobility separator is the scan speed in the region of the ion signal of interest.

6. The method according to claim 1, wherein a selection list which contains known isomers or isomers of particular analytical interest is used for the selection of the ion signal of interest from the ion signals of the first map.

7. The method according to claim 6, wherein the selection list depends on the type of substance mixture.

8. The method according to claim 1, wherein a user marks the ion signal of interest in a visual representation of the first map.

9. The method according to claim 8, wherein the extent of the marking in the direction of the mobility specifies the mobility resolution of the second map in the region of the ion signal of interest and determines the at least one parameter of the trapped ion mobility separator.

10. The method according to claim 1, wherein a mobility axis of the first and/or second map is calibrated and the mobility or collision cross-section of the ion signal of interest is determined.

11. The method according to claim 10, wherein known mobilities or collision cross-sections of identified substances of the substance mixture are used for the calibration.

12. The method according to claim 10, wherein known mobilities or collision cross-sections of reference substances which are added to the substance mixture are used for the calibration.

13. The method according to claim 12, wherein at least two reference substances whose mobilities encompass the mobility of the ion signal of interest are added to the substance mixture.

14. The method according to claim 1, wherein samples are separated by a substance separator, in particular a liquid chromatograph, and fed to the mass spectrometer.

15. The method according to claim 14, wherein an ion signal is only displayed in a visual representation of a mass-mobility map, or an ion signal of interest is only selected, when the ion signal has reached a maximum during the substance separation.

16. The method according to claim 1, wherein the method is worked out in detail with the aid of a first sample for a series of similar samples and is then used for the further samples in the same way.

* * * * *